US009149567B2

(12) United States Patent
Eng et al.

(10) Patent No.: US 9,149,567 B2
(45) Date of Patent: *Oct. 6, 2015

(54) POWDER-FREE ANTIMICROBIAL COATED GLOVE

(75) Inventors: Aik Hwee Eng, Petaling Jaya (MY); Hee Meng Lai, Melaka (MY); Kuang Leng Lim, Klang (MY); Koon Meow Ting, Klang (MY); David M. Lucas, Petaling Jaya (MY)

(73) Assignee: Ansell Limited, Victoria (AU)

( * ) Notice: Subject to any disclaimer, the term of this patent is extended or adjusted under 35 U.S.C. 154(b) by 203 days.

This patent is subject to a terminal disclaimer.

(21) Appl. No.: 12/720,146

(22) Filed: Mar. 9, 2010

(65) Prior Publication Data

US 2010/0233223 A1    Sep. 16, 2010

Related U.S. Application Data

(60) Provisional application No. 61/159,252, filed on Mar. 11, 2009.

(51) Int. Cl.
| | |
|---|---|
| *A01N 25/34* | (2006.01) |
| *A01N 37/52* | (2006.01) |
| *A01N 33/12* | (2006.01) |
| *A61K 31/085* | (2006.01) |
| *A61K 31/08* | (2006.01) |
| *A01N 31/14* | (2006.01) |
| *A01N 31/02* | (2006.01) |
| *A01N 59/16* | (2006.01) |
| *B05D 3/00* | (2006.01) |
| *A01P 1/00* | (2006.01) |
| *A01P 3/00* | (2006.01) |
| *A61L 31/16* | (2006.01) |
| *A61L 31/10* | (2006.01) |
| *A61L 31/14* | (2006.01) |
| *A41D 19/00* | (2006.01) |

(52) U.S. Cl.
CPC ............... *A61L 31/16* (2013.01); *A61L 31/10* (2013.01); *A61L 31/145* (2013.01); *A41D 19/0055* (2013.01); *A41D 2400/34* (2013.01); *A61L 2300/404* (2013.01); *A61L 2300/608* (2013.01); *A61L 2300/622* (2013.01)

(58) Field of Classification Search
None
See application file for complete search history.

(56) References Cited

U.S. PATENT DOCUMENTS

| | | | |
|---|---|---|---|
| 3,516,941 A | 6/1970 | Matson | |
| 3,830,035 A * | 8/1974 | Hoover | ............................ 53/460 |
| 4,102,806 A | 7/1978 | Kondo et al. | |
| 4,328,119 A | 5/1982 | Iwasaki et al. | |
| 4,853,978 A | 8/1989 | Stockum | |
| 4,898,633 A | 2/1990 | Doree et al. | |
| 5,089,205 A | 2/1992 | Huang et al. | |
| 5,133,090 A | 7/1992 | Modak et al. | |
| 5,138,719 A | 8/1992 | Orlianges et al. | |
| 5,284,607 A | 2/1994 | Chen | |
| 5,357,636 A | 10/1994 | Dresdner, Jr. et al. | |
| 5,483,697 A | 1/1996 | Fuchs | |
| 5,486,322 A | 1/1996 | Fuchs | |
| 5,570,475 A | 11/1996 | Nile et al. | |
| 5,708,023 A | 1/1998 | Modak et al. | |
| 5,827,531 A | 10/1998 | Morrison et al. | |
| 5,965,610 A | 10/1999 | Modak et al. | |
| 6,019,922 A | 2/2000 | Hassan et al. | |
| 6,037,386 A | 3/2000 | Modak et al. | |
| 6,159,457 A * | 12/2000 | Mougin | ..................... 424/78.03 |
| 6,195,805 B1 | 3/2001 | Bourne et al. | |
| 6,347,408 B1 | 2/2002 | Yeh | |
| 6,378,137 B1 | 4/2002 | Hassan et al. | |
| 6,391,409 B1 | 5/2002 | Yeh-Siung et al. | |
| 6,716,895 B1 | 4/2004 | Terry | |
| 6,846,846 B2 | 1/2005 | Modak et al. | |
| 6,890,653 B2 | 5/2005 | Wulff et al. | |
| 7,032,251 B2 | 4/2006 | Janssen | |
| 7,563,461 B2 | 7/2009 | Modak et al. | |
| 7,820,284 B2 | 10/2010 | Terry | |
| 8,137,735 B2 | 3/2012 | Wang et al. | |
| 2003/0204893 A1 | 11/2003 | Chou | |
| 2004/0048771 A1 | 3/2004 | McDermott et al. | |
| 2004/0091504 A1 | 5/2004 | Hamann | |
| 2004/0102429 A1 | 5/2004 | Modak et al. | |
| 2004/0115250 A1 | 6/2004 | Loo et al. | |
| 2004/0157073 A1 | 8/2004 | Burrell et al. | |
| 2004/0219227 A1 | 11/2004 | Modak et al. | |
| 2004/0247685 A1 | 12/2004 | Modak et al. | |

(Continued)

FOREIGN PATENT DOCUMENTS

| | | |
|---|---|---|
| CN | 101163455 | 4/2008 |
| EP | 0300814 A2 | 1/1989 |

(Continued)

OTHER PUBLICATIONS

Preliminary Report on Patentability and Written Opinion of the International Searching Authority mailed Sep. 22, 2011 for PCT Application No. PCT/US2010/026783.

(Continued)

*Primary Examiner* — Mina Haghighatian
*Assistant Examiner* — Erin Hirt
(74) *Attorney, Agent, or Firm* — Moser Taboada

(57) ABSTRACT

Provided herein are powder-free elastomeric articles exhibiting good antimicrobial and anti-blocking properties. Also provided herein are methods for the manufacture of such articles substantially free from antimicrobial interfering materials, as well as packaging means for maintaining antimicrobial efficacy.

27 Claims, No Drawings

(56) References Cited

U.S. PATENT DOCUMENTS

| | | |
|---|---|---|
| 2005/0002995 A1* | 1/2005 | Schaller .................. 424/443 |
| 2005/0019431 A1 | 1/2005 | Modak et al. |
| 2005/0035493 A1 | 2/2005 | Flather et al. |
| 2005/0048138 A1 | 3/2005 | Perrier et al. |
| 2005/0066414 A1 | 3/2005 | Yu et al. |
| 2005/0081278 A1 | 4/2005 | Williams |
| 2005/0112180 A1 | 5/2005 | Chou |
| 2005/0127552 A1 | 6/2005 | Modha et al. |
| 2005/0186258 A1 | 8/2005 | Wang et al. |
| 2005/0238602 A1 | 10/2005 | Modak et al. |
| 2005/0281762 A1 | 12/2005 | Modak et al. |
| 2006/0059604 A1 | 3/2006 | Lai et al. |
| 2006/0070167 A1 | 4/2006 | Eng et al. |
| 2006/0150300 A1 | 7/2006 | Hassan et al. |
| 2007/0020342 A1* | 1/2007 | Modak et al. ............ 424/642 |
| 2007/0104766 A1 | 5/2007 | Wang et al. |
| 2007/0118967 A1 | 5/2007 | Flather et al. |
| 2008/0020023 A1* | 1/2008 | Wang et al. ............. 424/443 |
| 2009/0042950 A1 | 2/2009 | Pandya |

FOREIGN PATENT DOCUMENTS

| | | | |
|---|---|---|---|
| EP | 1247851 A1 | 9/2002 | |
| JP | 2009-538961 | 11/2009 | |
| WO | WO92/06143 | * 4/1992 | ............ C09D 5/20 |
| WO | WO-98/29501 | 7/1998 | |
| WO | WO-2005/060856 A1 | 7/2005 | |
| WO | WO-2007/142629 A1 | 12/2007 | |

OTHER PUBLICATIONS

Shintre, Milind S., et al., "Efficacy of an alcohol-based healthcare hand rub containing synergistic combination of farnesol and benzethonium chloride", *International Journal of Hygiene and Environmental Health 209*, (2006), 477-487 pgs.

Modak, Shanta et al., "A Topical Cream Containing a Zinc Gel (Allergy Guard) as a Prophylactic against Latex Glove-Related Contact Dermatitis", *Dermatitis*, vol. 16, No. 1, (Mar. 2005), 22-27 pgs.

Shintre, Milind S., et al., "Evaluation of an Alcohol-Based Surgical Hand Disinfectant Containing a Synergistic Combination of Farnesol and Benzethonium Chloride for Immediate and Persistent Activity Against Resident Hand Flora of Volunteers and With a Novel in Vitro Pig Skin Model", *Infection Control and Hospital Epidemiology*, vol. 28, No. 2, (Feb. 2007), 191-197 pgs.

PCT International Search Report/Written Opinion in PCT/US10/26783, dated Apr. 29, 2010, 10 pp.

Second Office Action from the Chinese Patent Office dated Jan. 24, 2014 for corresponding Chinese Patent Application No. 201080019053.8, 16 pages.

Japanese Office Action for Patent Application No. P2011-554138 dated Nov. 26, 2013; 6 pages.

* cited by examiner

POWDER-FREE ANTIMICROBIAL COATED GLOVE

CROSS-REFERENCE TO RELATED APPLICATIONS

This application claims priority under 35 U.S.C. §119 (e) to U.S. Patent Application Ser. No. 61/159,252, filed Mar. 11, 2009, which is hereby incorporated by reference in its entirety.

TECHNICAL FIELD

The present invention generally relates to elastomeric articles, such as gloves, particularly gloves for use in the medical profession that has an antimicrobial gel coating protected with an anti-blocking surface film.

BACKGROUND

Skin-contacting articles, such as gloves, particularly medical gloves, are commonly used as a protective barrier against the contamination of the user by chemicals and body fluids containing microorganisms including bacteria and/or viruses and the like. As such, these gloves and other skin-contacting articles are manufactured in such a way that they are entirely impermeable to the contaminants or microorganisms during use. However, medical gloves are typically extremely thin, manufactured from soft elastomeric materials such as natural or synthetic rubbers and may puncture or rupture during use, allowing microorganisms to pass through the discontinuity in the glove.

One approach to this problem has been the application of antimicrobial coatings to the elastomeric articles. For example, U.S. Pat. No. 4,853,978 (Stockum) discloses a natural rubber surgical glove having an inner coating containing the cationic antimicrobial agents chlorhexidine gluconate (CHG) or polyhexamethylene biguanide hydrochloride (PHMB). Cross-linked cornstarch is included in the inner coating as an anti-blocking agent, which is also said to affix the CHG and PHMB in place and allow their slow release during perspiration. However, the use of cross-linked cornstarch is not compatible with the trend towards powder-free medical environments.

U.S. Pat. No. 5,089,205 (Huang) discloses natural latex gloves having an inner lubricant layer containing chlorhexidine diacetate. Again, powdered starch is disclosed as an anti-blocking agent. Although the patent teaches modifying the chlorhexidine with an anionic or nonionic surfactant to render it compatible with anionic components of the gloves, no mention is made of the effect of the surfactant on antimicrobial efficacy since the anionic or non-ionic surfactant (which has both anionic and cationic counter parts that have equivalent charges) will clearly neutralize the chlorhexidine cationic antimicrobial agent.

U.S. Pat. No. 5,133,090 (Modak et al.) discloses a latex glove having an inner coating of chlorhexidine and a lubricating agent, such as zinc oxide, hydroxycellulose or corn starch. Corn starch can be used provided it has been modified with a surfactant to block adsorption sites for the chlorhexidine. Again use of corn starch does not result in a powder free surgical glove.

U.S. Pat. No. 5,483,697 (Fuchs) discloses a double-layer latex glove having an inner layer, an outer layer sealing a middle layer comprising an antimicrobial agent in the form of a solution, which may be mixed with a hydrogel. The hydrogel is said to physically block or plug holes that form in the inner and outer layers. Examples of hydrogels include corn starch and derivatives of cellulose. No mention is made of the effect of the hydrogel on the efficacy of the antimicrobial agent. The antimicrobial agent is not delivered to the hand of the user killing any germs present, rather guards against any microbes present in a sharp instrument when the outer surface of the glove is breached. Clearly, the kill time of the microbes becomes an extremely important factor to produce effective kill since the outer glove breach occurs in a short time frame.

U.S. Pat. No. 5,570,475 (Nile et al.) discloses a surgeon's glove having a polymeric donning layer disposed thereon comprising a polymer of specific repeating units. The polymeric layer preferably has raised domains. No mention is made of any antimicrobial agent or the potential effect of the polymer layer on its efficacy.

U.S. Pat. No. 6,391,409 (Yeh et al.) discloses a powder free nitrile-coated natural rubber glove having an intermediate layer comprised of a synthetic rubber and nitrile rubber. The intermediate layer is said to aid donning and prevent self-sticking of the inner glove surfaces. No mention is made of any antimicrobial agent or the potential effect of the intermediate layer on its efficacy.

U.S. Pat. No. 6,378,137 (Hassan et al) discloses a powder-free polymeric medical glove having an outer side silicone-treated surface and an inner side bonded to anti-blocking layer formed from a polymer/copolymer, a high density polyethylene particle, and a wax, the anti-blocking layer coated with a layer of silicone emulsion. No mention is made of any antimicrobial agent or the potential effect of the anti-blocking layer on its efficacy.

U.S. Pat. No. 7,032,251 (Janssen) discloses an elastomeric article having a donning layer comprising a polymeric coating cross-linked with a polyamine epichlorohydrin crosslinking agent. The polymeric coating may comprise cellulose derivatives. No mention is made of any antimicrobial agent or the potential effect of the polymeric coating on its efficacy.

U.S. Patent Publication No. 2003/0204893 (Wang et al.) discloses an elastomeric glove having a preparation disposed on the interior surface of the glove comprising an acidic antimicrobial substance and buffer that resists pH change. The preparation may also comprise thickeners, which include cellulose derivatives. No mention is made of the tackiness or blocking properties of the preparation or the effect of the thickeners on the efficacy of the antimicrobial agent.

U.S. Patent Publication No. 2004/0115250 (Loo et al.) discloses an elastomeric glove having a moisturizing film comprising glycerol and a botanical extract, such as aloe vera and chamomile. The film may also comprise an anti-blocking wax. No mention is made of any antimicrobial agent or the potential effect of the wax on its efficacy.

U.S. Patent Publication No. 2005/0081278 (Williams) discloses an elastomeric glove having a dried lotion coating on the inside skin-contacting surface comprising a film-forming compound and an oil-based emollient. Film forming compounds include polyurethane, acrylonitrile, neoprene, acrylic latex styrene butadiene rubber and polyisoprene. Antimicrobial agents may be present in the coating, but only in amounts sufficient to act as preservatives. No mention is made of the tackiness of the coating, which will lead to blocking of the glove interior surfaces or the efficacy of the antimicrobials within the coating.

U.S. Patent Publication No. 2005/0112180 (Chou) discloses an elastomeric glove having a first layer comprising an antimicrobial agent and a second hand-contacting layer configured to resist penetration by the antimicrobial agent. The interior surface of second layer may be provided with a preparation comprising one or more of a second antimicrobial agent, a buffer, a moisturizer, a soothing agent and a thickener. No mention is made of the tackiness of the second layer preparation or its antimicrobial efficacy.

U.S. Patent Publication No. 2006/0059604 (Lai et al.) and U.S. Pat. No. 6,709,725 (Lai et al.) disclose latex gloves coated with a non-tacky aqueous polymeric emulsion comprising a film-forming polymer or copolymer, a wax, a surfactant and a hardness modifier. No mention is made of any antimicrobial agent or the potential effect of the polymeric emulsion on its efficacy.

U.S. Patent Publication No. 2006/0070167 (Eng et al.) discloses a rubber glove having a dried coating of an emulsified hand-friendly mixture comprising a water-soluble humectant moisturizer, a water-insoluble occlusive moisturizer, a water-soluble surfactant, and a water-soluble lubricant. The coating mixture may also contain an antimicrobial agent. The coating is said to be inherently non-tacky and non-blocking due to the fine dispersion of the water insoluble occlusive moisturizer within the dried coating and the coating is said to improve donning of the glove. No mention is made of the effect of the dried coating on the efficacy of the antimicrobial agent.

U.S. Patent Publication No. 2007/0104766 (Wang et al.) discloses a powder-free elastomeric article having a surface coating comprising an antimicrobial agent, hydrophilic film-forming polymer and a hydrophobic component. The non-volatile water-soluble antimicrobial agent is incorporated in a controlled-release matrix comprising a blend of a hydrophilic polymer and a hydrophobic component. The controlled-release matrix/blend requirements include: compatibility with the antimicrobial agent, formation of a reservoir of antimicrobial agent, coating film flexibility and lower water-solubility of the matrix/blend than that of the antimicrobial agent. The hydrophilic polymers include cellulosic polymers. The hydrophilic polymer is believed to provide a reservoir for the antimicrobial agent, while the hydrophobic component is believed to improve the film's flexibility through its plasticizing effect. The balance of hydrophilicity and hydrophobicity in the coating film is said to control the release of the antimicrobial agent. No mention is made of the tackiness of the surface coating.

Thus, there remains a need for powder-free elastomeric articles, such as medical gloves, which exhibit good antimicrobial and anti-blocking properties.

SUMMARY

The present invention provides powder-free elastomeric articles exhibiting good antimicrobial and anti-blocking properties. The antimicrobial composition is a gel that is coated on the interior surface of the glove, which if left uncoated, would subject the glove to blocking, wherein the interior surfaces of the glove stick together preventing easy donning of the glove. The interior surface of the glove with the antimicrobial gel coating is covered with a cellulose-based solid film that seals the antimicrobial gel preventing blocking of the glove. The cellulose-based film that covers the antimicrobial gel is capable of being dissolved easily by skin-generated moisture due to the unique properties of the cellulose-based containment film selected. Also provided herein are methods for the manufacture of such articles being durable and substantially free from antimicrobial interfering materials. In addition, packaging methods for maintaining antimicrobial and anti-blocking efficacy of the glove are provided.

Accordingly, one aspect of the present invention is directed to a powder-free antimicrobial elastomeric article, comprising:

an elastomeric layer having an interior surface and an exterior surface;

an antimicrobial gel coating applied to the interior surface of the elastomeric layer; and an anti-blocking film coating disposed on to the antimicrobial gel coating.

Generally, the antimicrobial gel coating comprises a coating formulation containing one or more water-soluble antimicrobial agents. In some embodiments, the antimicrobial agent(s) are contained in a zinc gel formulation comprising a mixture of irritant-inactivating amounts of soluble zinc salts. The antimicrobial agents present in the zinc gel formulation can include, in one or more embodiments, chlorhexidine gluconate (CHG), polyhexamethylene biguanide hydrochloride (PHMB), benzethonium chloride (BZT), farnesol, and octoxyglycerin. These compositions are gel-like even in the dried condition on the internal surfaces of a glove, and thus, if left uncoated the gloves would become blocked, making donnability poor.

Generally, the anti-blocking film coating comprises a cellulose composition that exhibits inverse solubility versus temperature. That is, these cellulose compositions dissolve readily in cold water but form a liquid crystal gel network when exposed to a higher temperature forming a two-phase structure. The gel formed is extremely stable at high temperatures. The transition temperature is called 'lower critical solution temperature' or LCST. Cellulose compounds that exhibit this behavior include methyl cellulose, hydroxypropylcellulose, hydroxypropyl methyl cellulose (HPMC) and hydroxyethyl methyl cellulose (HEMC). The LCST temperature depends on concentration in solution and the molecular weight of the composition. Higher molecular weight has a higher level of gel formation and lower solubility in cold water. The solution containing a dissolved LCST compound is sprayed on the skin contacting surface of the glove with the antimicrobial gel coating and tumble dried at a temperature significantly greater than the LCST temperature. During the final drying process, the LCST film becomes a solid film covering the antimicrobial gel glove coating providing anti-blocking properties. The solid film formed will readily dissolve or disintegrate by the skin-generated moisture since the skin temperature is below the lower critical solution temperature LCST. This dissolution immediately releases the glove coating. The film strength may be improved by additives such as dicalcium phosphate dihydrate. In an embodiment, the anti-blocking film coating optionally comprises a water-insoluble occlusive moisturizer.

One or more additional elastomeric layers may be provided. In addition, one or more functional coatings, such as a slip coating (also referred to as a donning coating), may be provided between the elastomeric layer and the antimicrobial gel coating. A slip layer may comprise a polymer coating that is, for example, polyurethane-based or acrylic-based. Wax particles can be added to the polymer coating for further ease in donnability. A micro-roughness textured surface is another way to provide a slip coating.

The article can be packaged in such a way as to preserve its antimicrobial activity as well as anti-blocking behavior of the glove during transportation and storage. In an embodiment, the article is packaged in an inner wrap surrounded by an outer pack. The size of the inner wrap, after folding, is generally smaller than the outer pack for easy sealing. The pack is sealed such that a sufficient volume of air is present to provide a cushioning effect to the inner wrap containing the article. This cushioning air layer prevents undue pressure on the solid film that is covering the antimicrobial gel coating on the interior skin contacting surface of the glove.

Another aspect of the present invention is directed to a process for preparing a powder-free antimicrobial elastomeric article, comprising:

providing an elastomeric layer having an interior surface and an exterior surface;

applying an antimicrobial gel coating comprising one or more antimicrobial agents to the interior surface of the elastomeric layer; and drying the antimicrobial gel coating; and applying an anti-blocking film coating to the antimicrobial gel coating.

A detailed embodiment provides that the resulting gloves exhibit no loss of antimicrobial activity following aging at 50° C. for 8 weeks, or 40° C. for 6 months.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

The present invention provides powder-free elastomeric articles exhibiting good antimicrobial and anti-blocking properties. Applicants have surprisingly found that application of an anti-blocking coating to an antimicrobial gel coating on an elastomeric glove not only prevents blocking, but there is no interference with antimicrobial efficacy during use and antimicrobial activity is maintained during storage.

Accordingly, one aspect of the present invention is direct to a powder-free antimicrobial elastomeric article, comprising:

an elastomeric layer having an interior surface and an exterior surface;

an antimicrobial gel coating applied to the interior surface of the elastomeric layer; and an anti-blocking film coating applied to the antimicrobial gel coating.

The gloves provide stable antimicrobial efficacy, meaning that antimicrobial agent efficacy remains stable with no or little deterioration after the glove has been stored over the period of shelf-life of the glove, as indicated in a accelerated aging test, i.e. gloves exhibit no loss of antimicrobial activity following aging at 50° C. for 8 weeks and 40° C. for 6 months. The gloves also exhibit anti-blocking behavior after aging.

In a specific embodiment, the anti-blocking film coating comprises a cellulosic water-soluble polymer; and the drying step comprises: drying the anti-blocking film coating at a temperature greater than the low critical solution temperature of the cellulosic water-soluble polymer to form a liquid film, and further drying of the liquid film to form a solid film covering said antimicrobial gel coating.

By "powder-free" is meant an elastomeric article that has little or no powder or cross-linked starch. According to ASTM D 6124-01, the glove must have less than about 2 mg of powder or "any water insoluble, filter retained residue" per article.

By "interior surface" is meant the surface of the article that contacts the wearer. By "exterior surface" is meant the surface that contacts the atmosphere.

The elastomeric article can be any article intended to contact human skin, such as medical articles, including gloves, condoms, finger stalls, and the like. Latex used to prepare the articles can be provided in aqueous emulsions or solvent-based emulsions.

Suitable elastomers for use in the elastomeric layer include natural rubber latexes, such as Hevea and Guayule latexes, as well as synthetic latexes, such as polychloroprene, carboxylated acrylonitrile butadiene, polyisoprene, polyurethane, styrene-butadiene, and the like. Blends of natural and synthetic latexes may also be used.

The elastomeric layer can be provided with a textured inner surface having micro-roughness for enhanced donning characteristics. The elastomeric layer can also be provided, alone or in conjunction with the textured inner surface, with a textured outer surface for enhanced grip characteristics. Methods for forming such textured elastomeric surfaces are provided in U.S. Patent Application Publication Nos. 2005/0035493 (Flather), 2007/0118967 (Flather), and 2006/0150300 (Hassan), the contents of each of which are hereby incorporated by reference in their entireties.

The antimicrobial coating applied to the interior surface of the elastomeric layer can be any coating that kill or inhibit the growth of microorganisms, including bacteria, viruses, fungi, molds, and the like. Generally, the antimicrobial gel coating comprises a coating formulation containing one or more soluble antimicrobial agents. Suitable antimicrobial agents include biguanides such as chlorhexidine salts (e.g., Gluconate salt CHG) and polyhexamethyl biguanide (PHMB), quarternary ammonium salts, such as benzalkonium chloride (BZK) and benzethonium chloride (BZT), chlorinated phenols, such as triclosan, essential oils, such as farnesol, phenoxyethanol, octoxyglycerin, iodine compounds, silver salts, antifungal agents, and the like. Other antimicrobial agents can be found in such references as Goodman and Gilman's *The Pharmacological Basis of Therapeutics* (McGraw-Hill, 2005), the content of which is hereby incorporated by reference in its entirety.

In some particular embodiments, the antimicrobial agent(s) are contained in a zinc gel formulation comprising a mixture of irritant-inactivating amounts of water-soluble zinc salts (such as zinc gluconate, zinc acetate and zinc lactate), panthenol, and a gelling agent (such as polyquaternium 10). The concentration of each zinc salt is generally between about 0.2 and 7% w/w. The antimicrobial agents present in the zinc gel formulation preferably include CHG, PHMB, BZT, farnesol and octoxyglycerin. Other ingredient, such as surfactants, emulsifiers, stabilizers, emollients, humectants, and silicone polymers, may be present. Specific zinc gel/antimicrobial formulations for use in the present invention can be found in Modak et al., U.S. Pat. Nos. 6,846,846, 6,037,386, 5,965,610 and 5,708,023; U.S. Patent Application Publication Nos. 2007/0020342, 2005/0281762, 2005/0238602, 2005/0048138, 2005/0019431, 2004/0247685, 2004/0219227 and 2004/0102429; and *Infect. Control Hosp. Epidemiol.* 28:191-197 (2007), *Int. J. Environ. Health* 209:477-487 (2006) and *Dermatitis* 16:22-27 (2005), the content of each of which is hereby incorporated by reference in its entirety.

The antimicrobial coating is generally formed from an aqueous solution wherein the water is substantially removed during processing. In a detailed embodiment, the aqueous solution comprises, in weight %, polyquaternium 10 in an amount in the range of 0.01-1%, zinc lactate in an amount in the range of 0.01 to 3%, zinc acetate in an amount in the range of 0.01% to 3%, zinc gluconate in an amount in the range of 0.01 to 3%, chlorhexidine gluconate in an amount in the range of 1 to 5%, phenoxyethanol in an amount in the range of 0.01 to 3%, benzethonium chloride in an amount in the range of 0.01 to 1%, Teric N100 (nonyl phenol condensed with 100 ethylene oxide units) in an amount in the range of 0.1 to 5%, octoxyglycerin in an amount in the range of 0.1 to 5%, d-panthenol in an amount in the range of 0.1 to 2%, a solubilizer in an amount in the range of 0.1 to 3%, farnesol in an amount in the range of 0.1 to 2%, aminofunctional siloxane in an amount in the range of 0.1 to 3%, and water in an amount in the range of 70-90%.

In one or more embodiments, the antimicrobial agents may be provided in an encapsulated form or surrounded by a capsule or coating. Various encapsulation processes for forming a capsule or coating around substances have been developed and include processes which encapsulate ingredients by physical methods and/or chemical methods. Processes for encapsulating water soluble ingredients using a water insoluble capsule or hydrophobic shell are also known in the art. For example, U.S. Pat. No. 6,890,653, describes microcapsule dispersions having a capsule core comprising water-soluble organic substances and a capsule coating of polyurethane and/or polyurea in a hydrophobic solvent. U.S. Pat. No. 5,827,531 describes a process for forming multi-layered microcapsules that include alternating hydrophilic and hydrophobic liquid layers, surrounded by flexible, semi-permeable hydrophobic, outer membranes. One or more of the processes described in U.S. Pat. No. 5,827,531 rely on low shear mixing and liquid-liquid diffusion process. An alternative process is described in U.S. Pat. No. 4,102,806, which describes encapsulating core material which may be water-soluble or water-insoluble with an oleaginous material or "oil-and-fat" in an organic solvent. US Publication No. 2004/0048771 discloses an interfacial polymerization process to encapsulate an ingredient with an encapsulation wall made from a water-insoluble urea-formaldehyde polymer. The disclosures of U.S. Pat. Nos. 6,890,653, 5,827,531, and 4,102,806 and U.S. Patent Publication No. 2004/0048771 are incorporated by reference in their entireties.

Other processes for encapsulating water-insoluble ingredients are also known in the art. For example, U.S. Pat. No. 3,516,941 describes providing an aqueous solution of a water-insoluble ingredient to be encapsulated to a solution of water-soluble polymer in a reactor. The components are then subjected to high shear agitation that mixes the ingredient and polymer and breaks the ingredient down into very small bead-like capsules. A chemical catalyst is added to the mixture causing the polymer surrounds and forms a shell around each bead of the ingredient to be encapsulated. U.S. Pat. No. 4,328,119 discloses encapsulating hydrophobic core material by depositing an anion-modified aminoaldehyde resin on the core material. The disclosures of U.S. Pat. Nos. 3,516,941 and 4,328,119 are incorporated by reference in their entireties.

The anti-blocking coating applied to the antimicrobial gel coating can be any coating that prevents or inhibits the tackiness normally associated with the antimicrobial gel coating. Moreover, the nature of the coating is such that it is flexible enough not to flake or crack during storage despite its presence on an elastomeric material. When the article is a glove, the anti-block coating prevents blocking (sticking) of the interior of the gloves. In specific embodiments of the present invention, the anti-blocking coating is comprised of one or more cellulosic polymers, that are water-soluble, including hydroxypropylcellulose (HPC), hydroxypropylmethylcellulose (HPMC), methylcellulose (MC), and the like. The anti-block coating may additionally comprise other film-forming, water-soluble polymers such as polyvinylpyrrolidinone (PVP) and the like. In a detailed embodiment, the aqueous solution of anti-blocking coating comprises, in weight %, 1-10% HPC and 1-5% aminofunctional siloxane, or 0.1-5% HPMC.

The preferred cellulose compositions are hydroxypropylcellulose (HPC), hydroxypropylmethylcellulose (HPMC) and methylcellulose (MC) since they exhibit inverse solubility phenomenon wherein the compound is readily soluble in water at temperatures below low critical solution temperature, LCST and form a liquid crystal gel network at temperatures above LCST. The gel stability only increases as the temperature is increased. As a result, the drying of the antimicrobial gel with protective LCST gel film results in progressively stronger gel that cures to a solid protective film. The LCST for HPC is 40 to 44° C. The LCST of HPMC can be reduced from this 40 to 44° C. range by the degree of methylation as detailed in WO/1998/029501. The anti-blocking coating can optionally further comprise a water-insoluble occlusive moisturizer that can include, but is not limited to, aminofunctional siloxane, polydimethylsiloxane (dimethicone), oleyl erucate, or combinations thereof. Again, the type of coating is limited only by the requirement that it not substantially inhibit the activity of the antimicrobial agent(s), which can be routinely determined by those of skill in the art.

Hydroxypropylcellulose HPC is an ether of cellulose in which some of the hydroxyl groups in the repeating glucose units have been hydroxypropylated forming —OCH$_2$CH(OH)CH$_3$ groups. The average number of substituted hydroxyl groups per glucose unit is referred to as the degree of substitution (DS). Complete substitution would provide a DS of 3.

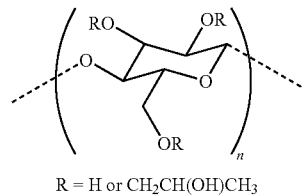

R = H or CH$_2$CH(OH)CH$_3$

Because the hydroxypropyl group added contains a hydroxyl group, this can also be etherified during preparation of HPC. When this occurs, the number of moles of hydroxypropyl groups per glucose ring, moles of substitution (MS), can be higher than 3. Because cellulose is very crystalline, HPC must have an MS about 4 in order to reach a good solubility in water. HPC has a combination of hydrophobic and hydrophilic groups, so it has a lower critical solution temperature (LCST) at 45° C. At temperatures below the LCST, HPC is readily soluble in water; above the LCST, HPC is not soluble. HPC forms liquid crystals and many mesophases according to its concentration in water. Such mesophases include isotropic, anisotropic, nematic and cholesteric.

Hydroxypropyl methylcellulose (HPMC) is a solid, and is a slightly off-white to beige powder in appearance and may be formed into granules. The compound forms colloids when dissolved in water and exhibits a thermal gelation property. That is, when the solution heats up to a critical temperature, the solution congeals into a non-flowable but semi-flexible mass. Typically, this critical (congealing) temperature is inversely related to both the solution concentration of HPMC and the concentration of the methoxy group within the HPMC molecule (which in turn depends on both the degree of substitution of the methoxy group and the molar substitution.

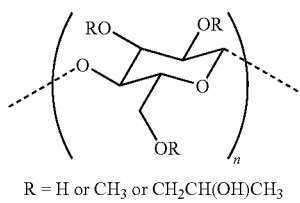

R = H or CH₃ or CH₂CH(OH)CH₃

That is, the higher is the concentration of the methoxy group, the lower is the critical temperature. The inflexibility/viscosity of the resulting mass, however, is directly related to the concentration of the methoxy group (the higher is the concentration, the more viscous or less flexible is the resulting mass).

Methyl cellulose (MC) is a chemical compound derived from cellulose. It is a hydrophilic white powder in pure form and dissolves in cold (but not in hot) water, forming a clear viscous solution or gel.

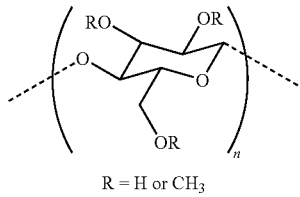

R = H or CH₃

Chemically, methyl cellulose is a methyl ether of cellulose, arising from substituting the hydrogen atoms of some of cellulose's hydroxyl groups —OH with methyl groups —CH3, forming —OCH3 groups. Different kinds of methyl cellulose can be prepared depending on the number of hydroxyl groups so substituted. Cellulose is a polymer consisting of numerous linked glucose molecules, each of which exposes three hydroxyl groups. The Degree of Substitution (DS) of a given form of methyl cellulose is defined as the average number of substituted hydroxyl groups per glucose. The theoretical maximum is thus a DS of 3.0, however more typical values are 1.3-2.6. Different methyl cellulose preparations can also differ in the average length of their polymer backbones. Methyl cellulose dissolves in cold water. Higher DS-values result in lower solubility, because the polar hydroxyl groups are masked. The chemical is not soluble in hot water, which has the paradoxical effect that heating a saturated solution of methyl cellulose will turn it solid, because methyl cellulose will precipitate out. The temperature at which this occurs depends on DS-value, with higher DS-values giving lower precipitation temperatures.

Without being bound by any particular theory, it is believed that the antimicrobial agents in the antimicrobial gel coating migrate from the interior surface of the article to the user's skin upon hydration and/or rubbing action of the anti-blocking coating, thereby providing antimicrobial protection to the user against microorganisms. Following removal of the article, the coatings can provide a soft and smooth feel to the user's skin.

The elastomeric article may also comprise conventional latex compounding additives and modifiers, including surfactants, wetting agents, antioxidants, antistatic agents, antifoaming agents, anti-webbing agents, pH modifiers, viscosity modifiers, thickeners, plasticizers, pigments, fillers, vulcanizing agents, activators, crosslinkers, accelerators, and the like.

The elastomeric article can be packaged in such a way as to preserve its antimicrobial activity during transportation and storage. In a preferred embodiment, the article is packaged in an inner wrap surrounded by an outer pack. These wraps may be made from paper, wax coated paper, polymer coated paper or polymeric sheet films that are well known in the art. The size of the inner wrap, after folding, is generally smaller than the outer pack for easy sealing. The pack is sealed such that a sufficient volume of a gas such as air is present to provide a cushioning effect to the inner wrap containing the article (a so-called "puffy pack"). In this manner, the inner wrap containing the article can move freely when the outer pack is held and shaken.

The powder-free antimicrobial elastomeric article can be prepared by a process comprising, providing an elastomeric layer having an interior surface and an exterior surface;

applying an antimicrobial gel coating to the skin-contacting surface of the article;

drying the antimicrobial gel coating;

applying an anti-blocking coating to the antimicrobial gel coating;

drying at a temperature sufficient to form liquid crystal gel and dry the gel to form a continuous solid film.

As noted above, one or more additional layers or coatings may be applied between the elastomeric layer and the antimicrobial gel coating, such as a slip coating.

When the elastomeric article is a glove, conventional dip methods may be employed, which include on-line processes for mass production of latex gloves. Generally, these methods involve forming the layers of the glove by, for example, dipping a pre-heated former into an aqueous coagulant, drying the coagulant on the former, dipping the former into a latex solution comprising natural and/or synthetic elastomers, and leaching the gelled latex in hot water. These steps can be repeated to build up elastomeric layers of the glove. If desired a second polymeric coating such as polyurethane may be applied to the skin contacting surface of the glove. The gloves are then cured. The outside surface of the gloves are then optionally treated chemically, such as by chlorination, to reduce tackiness. If chlorinated, the gloves are then washed.

The antimicrobial and anti-block coatings can then applied to the cured elastomeric gloves. In specific embodiments, the elastomeric gloves are washed off-line prior to application of the antimicrobial gel coating. This reduces antimicrobial interfering materials. The gloves are then optionally dried with a blower or drier prior to application of the antimicrobial and anti-block coatings by, for example, spraying tumbling or dipping. The antimicrobial gel coating can then be coated onto the glove surface by spraying and drying in a dryer through one or more nozzles. The anti-block composition is sprayed on the dried gloves with the antimicrobial coating and dried at a temperature greater than the LCST temperature of the cellulose composition to facilitate liquid crystal film formation and dying the film to form a continuous solid film that covers the antimicrobial gel coating preventing blocking of the interior surfaces of the glove. The final glove products are then inverted such that the antimicrobial gel coating is located on the interior side of the glove, and packaged in pairs, sterilized with gamma radiation, and cooled to room temperature.

In embodiments which utilize encapsulated antimicrobial agents, various methods of attaching or adhering encapsulated ingredients to a surface that are also known in the art may be incorporated in the processes described herein. Methods of attaching or adhering encapsulated ingredients to a surface are know in the art. For example, U.S. Pat. No. 5,138, 719 describes forming a solution of latex containing microcapsules and applying a layer of the latex to the surface of a glove by immersing the glove into the solution, followed by vulcanizing or hardening the formed layers. In one or more embodiments, the encapsulated antimicrobial agents may be bonded to the surface of a glove. U.S. Pat. No. 4,898,633 describes coating the surface of a substrate with a binder resin having microcapsules dispersed therein. U.S. Patent Publication No. 2005/0066414 discloses bonding encapsulated antimicrobial agents to a surface using a polymer, for example, polyurethane. U.S. Pat. Nos. 5,138,719, 4,898,633 and U.S. Patent Publication No. 2005/0066414 are incorporated by reference in their entireties.

Specific embodiments according to the methods of the present invention will now be described in the following examples. The examples are illustrative only, and are not intended to limit the remainder of the disclosure in any way.

EXAMPLES

Example 1

Antimicrobial Efficacy of Gloves

Natural rubber latex gloves containing a coating of polyurethane were prepared by the conventional dip method previously discussed from an aqueous emulsion of latex. The gloves were stripped from the formers and washed in water at 30 to 95° C. for 1 hour and dried. The gloves were then inverted and subjected to a second wash in water 30 to 95° C. for 1 hour and dried as described above. The gloves were then coated with an antimicrobial gel and dried in a tumbling dryer, followed by an anti-blocking coating. The anti-blocking coating is dried at a temperature greater than the LCST temperature of the cellulose composition to promote liquid crystal film formation and drying the film to a solid continuous film covering the antimicrobial gel coating. The composition of the antimicrobial gel coating is shown in Table 1, and the composition of the anti-blocking coating is shown in Table 2.

TABLE 1

| Ingredient | % Active in Formulation (wt/wt) |
|---|---|
| Ucare JR-30M, 100% Active (Polyquaternium 10) | 0.01-1% |
| Zinc Lactate, 100% Active | 0.01-3% |
| Zinc Acetate, 100% Active | 0.01-3% |
| Zinc Gluconate, 100% Active | 0.01-3% |
| Chlorhexidine Gluconate, 100% Active | 1-5% |
| Phenoxyethanol, 100% Active | 0.01-3% |
| Benzethonium Chloride, 100% Active | 0.01-1% |
| Teric N100, 100% Active (nonyl phenol condensed with 100 ethylene oxide units) | 0.1-5% |
| Sensiva SC-50, 100% Active (Octoxyglycerin) | 0.1-5% |
| D-Panthenol, 100% Active | 0.1-2% |
| Symrise Solubilizer 660352, 100% Active | 0.1-3% |
| Farnesol, 100% Active | 0.1-2% |
| DC939 Emulsion (Aminofunctional siloxane) | 0.1-3% |
| Water | 70-90% |

[1]Water is substantially removed during processing

TABLE 2

| Ingredient | % Active in Formulation (wt/wt) |
|---|---|
| DC939 Emulsion (Aminofunctional siloxane) | 1-5% |
| Klucel LF (Hydroxypropylcellulose) | 1-10% |
| Water | Balance |

[1]Water is substantially removed during processing

The resulting final glove products had a powder level of less than 2 mg/glove. Following packaging in a puffy pack as described above and sterilization with gamma radiation, the gloves had excellent dry hand donnability, wet/damp hand donnability, double gloving, anti-blocking and no wet look properties with no compromise in unaged and aged tensile strength and stretch characteristics. In contrast, gloves packaged in an inner wrap surrounded by an outer pack in which excess air had been squeezed out ("control pack") exhibited severe blocking and wet look properties.

Samples of gloves, unaged and aged at 50° C. for 8 weeks and 40° C. for 6 months, were tested for antimicrobial activity against $S.$ $aureus$. A finger stall of the glove was cut and filled with a known concentration of the $S.$ $aureus$ microbe. After specified kill time interval, a portion of the liquid in the finger stall was sampled and cultured in an active medium to assess microbe content. A control glove without the antimicrobial coating was also tested in parallel. Results are shown below in Table 3 in log reduction of $S.$ $aureus$ after 2 min exposure time. The composition provides a net log reduction in microbes greater than 3, after subtracting the log reduction of the control glove.

TABLE 3

| Aging | Net log reduction in microbes* |
|---|---|
| None | 4.5 |
| 50° C. for 8 weeks | 4.4 |
| 40° C. for 6 months | 4.5 |

*Log reduction of sample glove - log reduction of control glove

As shown in Table 3, the gloves exhibited no deterioration in antimicrobial efficacy upon accelerated aging.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A powder-free, antimicrobial glove, for use on a user's hand, comprising:
    an elastomeric layer having an interior surface that contacts the hand and an exterior surface;
    an antimicrobial gel coating comprising one or more antimicrobial agents covering the interior surface of the elastomeric layer; and
    a solid film comprising a water-soluble polymer coating disposed on the antimicrobial gel coating and over-covering the interior surface, wherein the antimicrobial gel would dispose the glove to blocking in the absence of the film, wherein the film inhibits such blocking, wherein the anti-blocking film coating dissolves upon contact with moisture to release the antimicrobial gel coating onto the user's hand.

2. The glove of claim 1, wherein the elastomeric layer comprises a cured latex selected from the group consisting of natural latex, synthetic latex, and blends of natural and synthetic latex.

3. The glove of claim 2, wherein the synthetic latex is selected from the group consisting of polychloroprene, carboxylated acrylonitrile butadiene, polyisoprene, polyurethane, styrene-butadiene, and combinations thereof.

4. The glove of claim 1, wherein the antimicrobial gel coating comprises one or more antimicrobial agents selected from the group consisting of chlorhexidine gluconate (CHG), polyhexamethylene biguanide hydrochloride (PHMB), benzalkonium chloride (BZK), benzethonium chloride (BZT), triclosan, farnesol, phenoxyethanol, octoxyglycerin, iodine compounds, silver salts, antifungal agents, antiviral agents, and combinations thereof.

5. The glove of claim 1, wherein the one or more antimicrobial agents are encapsulated.

6. The glove of claim 5, wherein the one or more antimicrobial agents are contained within microcapsules having a hydrophobic shell.

7. The glove of claim 1, wherein the antimicrobial gel coating comprises a zinc gel formulation.

8. The glove of claim 7, wherein the zinc gel formulation comprises one or more water-soluble zinc salts, panthenol, and a gelling agent.

9. The glove of claim 1, wherein the anti-blocking film coating is cellulose-based, comprising a cellulosic water-soluble polymer.

10. The glove of claim 9, wherein the cellulosic water-soluble polymer of the antiblocking film coating is selected from the group consisting of hydroxylpropylcellulose (HPC), hydroxypropylmethylcellulose (HPMC), methyl cellulose (MC), and combinations thereof.

11. The glove of claim 9, the film coating comprising a heat-cured film of the water-soluble polymer, which has a lower critical solution temperature (LCST) greater than 40° C., the greater solubility of the film below the LCST permitting dissolution of anti-blocking film coating by skin-generated moisture.

12. The glove of claim 1 having less than 2 mg of powder.

13. The glove of claim 1, wherein an antimicrobial agent from the antimicrobial gel coating is released from the glove following dissolution of the anti-blocking film coating.

14. The glove of claim 1, wherein the antimicrobial gel coating exhibits a reduction in bacterial growth of at least 3 log following a 2 minute exposure.

15. The glove of claim 1, wherein the antimicrobial gel coating exhibits substantially no loss of antimicrobial activity following aging at 50° C. for 8 weeks and 40° C. for 6 months.

16. A packaged powder-free, antimicrobial article comprising the powder-free, antimicrobial glove of claim 1 packaged in an inner wrap surrounded by and sealed within an outer pack, wherein the outer pack is sealed to contain a cushioning amount of gas to allow the inner wrap to freely move within the outer pack.

17. A powder free, antimicrobial elastomeric article, for contacting a user's skin, comprising:
an elastomeric layer having an interior surface that contacts the hand and an exterior surface; an antimicrobial gel coating comprising one or more antimicrobial agents disposed on the interior surface of the elastomeric layer; and a solid film coating comprising a water-soluble polymer disposed on the antimicrobial gel coating and over-covering the interior surface, wherein the antimicrobial gel would dispose the article to blocking in the absence of the film, wherein the film inhibits such blocking, wherein the anti-blocking film coating dissolves upon contact with moisture to release the antimicrobial gel coating onto the user's skin.

18. The article of claim 17 in the form of a glove, wherein the elastomeric layer comprises a cured latex of natural rubber, the antimicrobial gel coating comprises polyquaternium 10, zinc lactate, zinc acetate, zinc gluconate, chlorhexidine gluconate (CRG), phenoxyethanol, benzethonium chloride (BZT), octoxyglycerine, farnesol, and panthenol; and the anti-blocking film coating comprises hydroxypropylcellulose.

19. A process for preparing a powder-free, antimicrobial glove comprising:
providing an elastomeric layer having an interior surface and an exterior surface;
providing an antimicrobial gel coating comprising one or more antimicrobial agents to the interior surface of the elastomeric layer;
applying an a water-containing anti-blocking film coating composition comprising a water-soluble polymer to the dry antimicrobial gel coating; and
drying the anti-blocking film coating to remove water and form the a solid anti-blocking film covering the antimicrobial gel coating.

20. The process of claim 19, wherein the anti-blocking film coating comprises a cellulosic water-soluble polymer; and the drying step comprises:
drying the anti-blocking film coating at a temperature greater than the low critical solution temperature of the cellulosic water-soluble polymer to form a liquid film, and
further drying of the liquid film to form a solid film covering said antimicrobial gel coating.

21. The process of claim 19, further comprising forming an additional elastomeric layer, or applying an additional coating, or both between the elastomeric layer and the antimicrobial gel coating.

22. The process of claim 19, further comprising water-washing the glove prior to applying the antimicrobial gel coating.

23. The process of claim 19, wherein the antimicrobial gel coating comprises polyquaternium 10, zinc lactate, zinc acetate, zinc gluconate, chlorhexidine gluconate (CHG), phenoxyethanol, benzethonium chloride (BZT), octoxyglycerine, farnesol and panthenol.

24. The process of claim 19, further comprising packaging the powder-free, antimicrobial glove in an inner wrap surrounded by and sealed within an outer pack, wherein the outer pack is sealed to contain a sufficient amount of gas to allow the inner wrap to freely move within the outer pack.

25. The process of claim 19, wherein the step of providing an elastomeric layer having an interior surface and an exterior surface comprises dipping a pre-heated former into a powder free coagulant composition, drying the coagulant composition on the former, dipping the former into a latex solution comprising natural and/or synthetic elastomers, and leaching the gelled latex on the former in hot water.

26. The glove of claim 9, wherein the anti-blocking film further comprises a water-insoluble occlusive moisturizer.

27. The glove of claim 26, wherein the water-insoluble occlusive moisturizer is aminofunctional siloxane, polydimethylsiloxane (dimethicone), oleyl erucate, or combinations thereof.

* * * * *